United States Patent
Han et al.

[11] Patent Number: 6,121,253
[45] Date of Patent: Sep. 19, 2000

[54] PROSTAGLANDIN CONJUGATES FOR TREATING OR PREVENTING BONE DISEASE

[75] Inventors: Yongxin Han, Kirkland; Robert N. Young, Senneville, both of Canada; Laurent Gil, Belo Horizonte, Brazil; Rejean Ruel, St. Lazare, Canada

[73] Assignee: Merck Frosst Canada & Co., Kirkland, Canada

[21] Appl. No.: 09/440,351

[22] Filed: Nov. 15, 1999

Related U.S. Application Data

[60] Provisional application No. 60/109,307, Nov. 20, 1998.

[51] Int. Cl.$^7$ ................. A61K 31/095; A61K 31/12; C07F 9/38
[52] U.S. Cl. ................. 514/102; 514/107; 562/20; 562/21; 556/405
[58] Field of Search ................. 514/75, 102, 107, 514/124, 125, 126, 127, 134; 562/8, 20, 21; 556/404, 405; 549/218

[56] References Cited

U.S. PATENT DOCUMENTS

| | | |
|---|---|---|
| 3,927,197 | 12/1975 | Monkhouse . |
| 3,975,404 | 8/1976 | Lincoln, Jr. et al. . |
| 4,018,892 | 4/1977 | Walsh . |
| 4,097,601 | 6/1978 | Schaaf . |
| 4,171,331 | 10/1979 | Biddlecom et al. . |
| 4,621,100 | 11/1986 | Lund et al. . |
| 4,761,406 | 8/1988 | Flora et al. . |
| 4,921,697 | 5/1990 | Peterlik et al. . |
| 5,071,655 | 12/1991 | Baylink . |
| 5,071,840 | 12/1991 | Ebetino et al. . |
| 5,118,667 | 6/1992 | Adams et al. . |
| 5,409,911 | 4/1995 | Tyler et al. . |

FOREIGN PATENT DOCUMENTS

| | | |
|---|---|---|
| 0 179 277 B1 | 11/1988 | European Pat. Off. . |
| 0 341 961 A1 | 11/1989 | European Pat. Off. . |
| 0 381 296 A1 | 8/1990 | European Pat. Off. . |
| 0 496 520 A1 | 7/1992 | European Pat. Off. . |
| 2-104593 | 4/1990 | Japan . |
| 2-138118 | 5/1990 | Japan . |
| WO 93/24496 | 12/1993 | WIPO . |
| 9406750 | 3/1994 | WIPO . |

OTHER PUBLICATIONS

Klenner et al, J. Cancer Res. Clin. Oncol., vol. 116 (1990), pp. 341–350, "Anticancer–agent–linked phosphonates with antiosteolytic and antineoplastic properties: . . . ".

Harvey et al., Prostaglandins in Bone Resorption, (1988) Chapt. 3—"IV. Effects on Bone Formation", pp. 36–41.

Jee et al., Bone & Mineral, vol. 15 (1991), pp. 33–55, "Long–term anabolic effects of prostaglandin–E2 on tibial diaphyseal bone in male rats".

Raisz et al., Ann. Rev. Physiol., vol. 43 (1981), pp. 225–238, "Hormonal control of skeletal growth".

Rodan, J. Cellular Biochem. Suppl. 0 (15, Part F), pp. 160, Abstract Q 018 (1991), "Cellular approaches to therapy for the prevention and treatment of osteoporosis".

Frost, Clinical Orthopedics & Related Research, vol. 143 (1979), pp. 227–244, "Basic Science and Pathology: Treatment of osteoporoses by manipulation of coherent bone cell populations".

Ueno et al., Bone, vol. 6 (1985), p. 79–86, "The effects of prostaglandin E2 in rapidly growing rats: depressed longitudinal and radial growth and increased metaphyseal hard tissue mass".

Jee et al., Calcif. Tissue Int., vol. 37 (1985), pp. 148–157, "The effects of prostaglandin E2 in growing rats: Increased metaphyseal hard tissue and cortico–endosteal bone formation".

*Primary Examiner*—Jean F Vollano
*Attorney, Agent, or Firm*—Anthony D. Sabatelli; Melvin Winokur

[57] ABSTRACT

This invention relates to prostaglandin-bisphosphonate conjugates. These conjugates are effective for treating or preventing bone diseases such as osteoporosis. These conjugates simultaneously deliver a prostaglandin agent for increasing bone formation and a bisphosphonate agent for inhibiting bone resorption.

18 Claims, No Drawings

PROSTAGLANDIN CONJUGATES FOR TREATING OR PREVENTING BONE DISEASE

This application claims priority to Ser. No. 60/190,307, filed Nov. 20, 1998.

BACKGROUND OF THE INVENTION

The compounds of the present invention are analogues of the natural prostaglandin $PGD_1$, and $PGD_2$, $PGE_2$, $PGE_1$ and $PGF_2$ alpha useful in the treatment of osteoporosis. Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally, the adjacent side chains are in the trans orientation. $PGE_2$ has the following stricture.

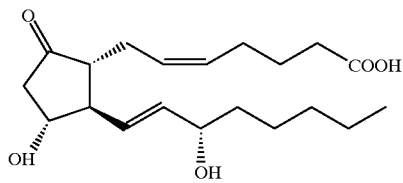

The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position. U.S. Pat. No. 4,171,331 teaches 1 and 2 substituted analogues of certain prostaglandins. Disclosed are trans 1 and 2 di(loweralkyl)phosphono; 1 and 2 chloro, bromo, and iodo; 1 and 2-thio; and 1 and 2 amino analogues of $PGE_1$.

U.S. Pat. No. 3,927,197 discloses the formation of various acid derivatives of prostaglandins such as amides, carboxylate-amine salts, and the 2-decarboxy-2-(2,3,4,5-tetryol-1-yl) derivative.

Osteoporosis is the most common form of metabolic bone disease and is commonly observed in postmemopausal women but also occurs in elderly males and females or in young individuals. Commonly, the disease is characterized by fractures of the wrist and spine, while femoral fractures are the dominant feature of senile osteoporosis. The physical causitive factor which creates susceptibility to fracturing is the gradual loss of bone. Apparently, the normal balance of bone resorption activity by the osteoclasts (bone dissolving or resorbing cells) and bone formation activity by the osteoblasts (bone forming cells) is disrupted by development of the disease so that the cavities created by the osteoclasts are not refilled by the osteoblasts. A number of pharmaceutical compounds are known in the art which hinder the activity of osteoclasts so that bone loss is diminished. For example, bisphosphonates as a class are useful in inhibiting bone loss and are therefore important in treating diseases associated with bone loss, including osteoporosis. A more difficult treatment regime or area has been the effective acceleration or stimulation of bone formation to maintain bone growth or strengthen weakened bones.

It is clear, however, that the activity of osteoblasts and osteoclasts is coordinated and regulated by a complex mechanism and is affected by a variety of hormones and prostaglandins. See Raisz et al., *Ann. Rev. Physiol.*, 43:225 (1981); U.S. Pat. No. 4,921,697 which teaches that inhibition of prostaglandin production by IFN-gamma is an effective treatment for osteoporosis and other bone-resorption diseases since prostaglandins have been implicated in bone loss or resorption. The literature also suggests that prostaglandins may also play an important role in bone formation. See W. Harvey and A. Bennett, "Prostaglandins in Bone Resorption" CRC Press, pp. 37 (1988). Osteoblasts are responsible for carrying out the bone formation process. It has been established that bone formation in vivo in animals is stimulated by systemic injection of $PGE_2$. See Rodan G. *J. Cell Biochem. Suppl.* 0 (15 Part F), 160 (1991).

The effects of prostaglandins administered alone has been disclosed in the art. Ueno et al., Bone, 6, 79–86, (1985) administered $PGE_2$ to rapidly growing rats at dosages of 1, 3 and 6 mg of $PGE_2$/Kg/day. The results showed an increase in hard tissue mass in the secondary spongiosa of the proximal tibial metaphysis and an increase in the number of trabeculae. Jee et al., Bone and Mineral, 15, 33–55 (1991), disclosed that subcutaneous injections of $PGE_2$ over 60, 120, and 180 days produced an increased tibial diaphyseal bone mass and elevated bone activity. The authors reported that the anabolic effects of $PGE_2$ increases periosteal and corticoendosteal bone mass and sustains the transient increase in bone mass with daily administration of $PGE_2$. It is known that very little control is possible over the duration and the concentration at which PGs reach the bone cells. It is also known that systemic injection or infusion of PGs is an alternative with significant drawbacks since the lungs efficiently remove PGs from circulation. See W. Harvey and A. Bennett, "Prostaglandins in Bone Resorption" CRC Press, pp. 37 (1988).

It is also known that toxicity of prostaglandins due to systemic distribution of the administered drug reduces or diminishes the pharmaceutical utility of these compounds. Delivery of high doses of prostaglandins which would be necessary because of the short half life of these compounds may cause unwanted side effects. Ueno et al reported that when $PGE_2$ was administered systemically through subcutaneous injections to rats, diarrhea and flushing of the extremities along with weight loss occurred at doses of 3 mg/Kg/day or higher. In addition, significant decreases in serum phosphate levels of 1 mg of $PGE_2$ were noted. Jee et al reported that long term administration of $PGE_2$ administered via subcutaneous injection resulted in soft tissue weight increases in adrenal glands, liver, kidneys, and lungs. U.S. Pat. No. 4,621,100 discloses side effects after oral dosing with $PGE_2$ including loose stools, diarrhea, vomiting, infected sclerae, and increased serum alkaline phosphatase levels.

Frost et al. in "Treatment of Osteoporosis by Manipulation of Coherent Bone Cell Populations", *Clinical Orthopedics and Related Research*, 143, 227 (1979) discloses a theoretical model that suggests it should be possible to synchronize the activity and metabolism of bone cells by administering bone cell activating agents first and then administering a bone resorption inhibiting agent. This proposed model assumes that bone formation inhibition does not take place, because no bone resorption inhibiting agent is administered during the bone formation phase of the bone remodeling unit. EPO App. No. 0 381 296 teaches the use of a kit wherein a bone activating period or treatment regime is followed by a bone resorption inhibiting regime. Examples of bone activating compounds cited in this reference include parathyroid hormone (PTH), inorganic phosphate, growth hormone, fluoride, thyroid hormone (e.g. thyroxin), certain vitamin D metabolites and prostaglandins ($PGE_2$ in a dose regime of 10 mg/kg per day). See also U.S. Pat. No. 5,118,667. Examples of bone resorption inhibiting polyphosphonates include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, propane-N,N-dimethyl-3-amino-1-hydroxy-1,1-diphosphonic acid, propane-3-3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid (administered after $PGE_2$ at a dosage per day of 0.005 mg P/kg), pentane-5-amino-1-hydroxy-1,1-diphosphonic acid, and hexane-6-amino-1-hydroxy-1,1-diphosphonic acid. Combinations of a methylene bisphosphonate coupled to a medicinal compound such as a Non-Steroidal Anti-Inflammatory Agent (NSAID) have been disclosed. See Japanese Patent Publication No. H2-104593.

U.S. Pat. No. 5,409,911, which issued on Apr. 25, 1995, describes prostaglandin-bisphosphonate compounds useful in treating bone disorders and is hereby incorporated by reference in its entirety. The compounds disclosed in U.S. Pat. No. 5,409,911 provide simultaneous delivery of a bone activating agent such as a prostaglandin that is chemically coupled to a bone resorption inhibiting compound which selectively delivers the bone activating agent to the target area. Upon gradual hydrolysis of the compound, the hydrolyzed products are able to provide bone resorption inhibiting activity (via the bisphosphonates) and bone growth or stimulating activity (via $PGE_2$).

The compounds of the present invention are also designed to deliver both a prostaglandin and a bisphosphonate to the target bone areas. However, the compounds of the present invention unexpectedly possess a critical balance of chemical stability and lability. These compounds possess the requisite stability to allow for their formulation into a finished pharmaceutical preparation, storage and shelf stability of the pharmaceutical preparation, and administration, and also the desired lability to permit the administered active ingredient to hydrolyze in vivo to release the prostaglandin and bisphosphonate components. The compounds of the present invention bind effectively to bone both in vitro and in vivo and liberate $PGE_2$ at an acceptable rate. The present invention also enables more effective delivery of $PGE_2$ to the target region and therefore overcomes the serious side effect disadvantages associated with administration of larger quantities of $PGE_2$ alone. In addition, $PGE_2$ administered systemically has a short half-life. The present invention overcomes the disadvantages prevalent in the background art and at the same time provides a compound that promotes bone growth and deters bone resorption to provide a treatment for osteoporosis and related disorders of calcium metabolism.

It is therefore an object of the present invention to provide novel prostaglandin-bisphosphonate conjugates.

It is another object of the present invention to provide such compounds having the ability to deliver a prostaglandin locally to bone and to gradually hydrolyze so that a bone resorption inhibitor and a bone formation enhancer can be delivered directly to bone.

It is another object of the present invention to provide methods for treating and or reducing the risk of contracting disease states or conditions associated with abnormal bone resorption.

It is another object of the present invention to provide methods for treating and or reducing the risk of contracting osteoporosis.

These and other objects will become readily apparent from the detailed description which follows.

SUMMARY OF THE INVENTION

The claimed invention's primary objective is to use compounds within the scope of the invention as chemical delivery agents of prostaglandins. This invention claims a novel chemical method for simultaneously delivering a bone formation enhancer such as a prostaglandin and a bone resorption inhibitor such as an amino bisphosphonate. The invention is a prostaglandin-bisphosphonate compound which when administered systemically has high affinity for bone. The compounds of the invention are then hydrolyzed to form a bisphosphonate and a prostaglandin. The invention is useful in the prevention and treatment of osteoporosis and has the distinct advantage that lower doses of prostaglandins may be administered to a mammal or patient in need thereof since the prostaglandin is delivered to the site of action before it is metabolized. This method also avoids the undesirable side affects associated with higher doses of prostaglandins. The invention is also directed to compounds of the following formula:

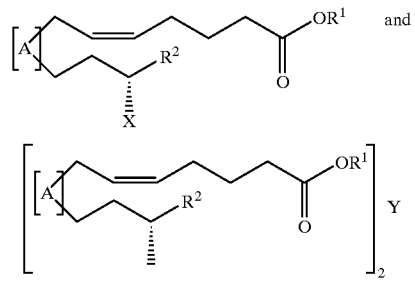

and mixtures thereof and the pharmaceutically acceptable salts thereof, wherein:

A is a dioxygenated cyclopentane moiety selected from the group consisting of:

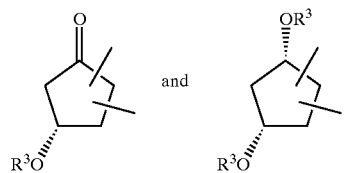

X is selected from the group consisting of:

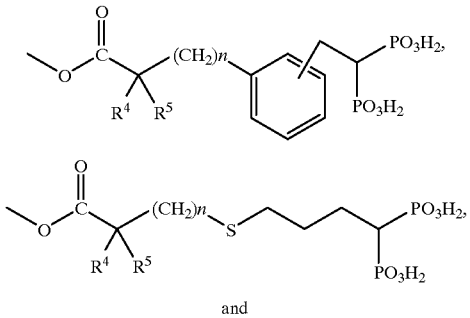

and

-continued

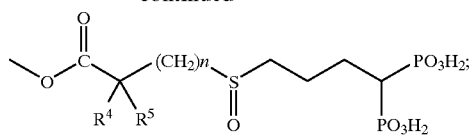

Y is selected from the group consisting of:

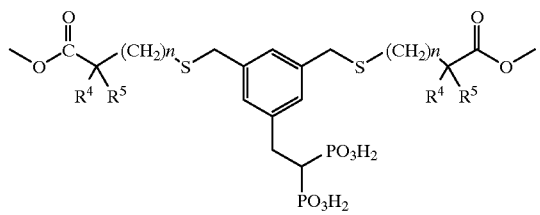

and

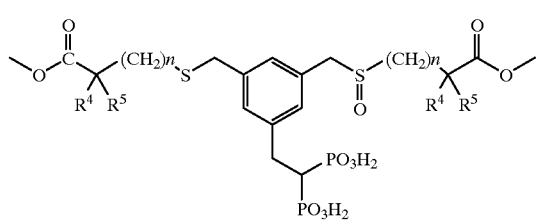

$R^1$ is selected from the group consisting of H, C1–C10 alkyl, and $Si(CH_3)_2tBu$;

$R^2$ is selected from the group consisting of H and $C_1$–$C_{10}$ alkyl;

$R^3$ is selected from the group consisting of H, tetrahydropyran, and $Si(CH_3)_2tBu$;

$R^4$ and $R^5$ are independently selected from the group consisting of H, C1–C10 alkyl, phenyl, benzyl, C1–C10 alkoxy, and $CF_3$, and n is an integer from 0 to 5.

The present invention also relates to pharmaceutical compositions comprising a therapeutically effective amount of the the compounds of the present invention and a pharmaceutically acceptable carrier.

The present invention also relates to a method of inhibiting bone resorption in a mammal comprising administering to a mammal in need thereof a therapeutically effective amount of the compounds of the present invention.

The present invention also relates to a method for treating or reducing the risk of contracting a disease state or condition associated with bone resorption comprising administering to said mammal a therapeutically effective amount of the compounds of the present invention.

The present invention also relates to a method of increasing the bone fracture healing rate in a mammal comprising administering to a mammal in need thereof a therapeutically effective amount of the compounds of the present invention.

The present invention also relates to a method for enhancing the rate of successful bone grafts in a mammal comprising administering to a mammal in need thereof a therapeutically effective amount of the compounds of the present invention.

The present invention also relates to a method for enhancing the rate of bone formation in a mammal comprising administering to a mammal in need thereof a therapeutically effective amount of the compounds of the present invention.

This invention is also directed to a method of treating or preventing osteoporosis by administering a pharmaceutically effective amount of the compound according to the present invention. It is directed to a method of increasing the bone fracture healing rate in a mammal exhibiting a bone fracture by systemically administering a pharmaceutically effective amount of the compound according to the present invention and to method for enhancing the rate of successful bone grafts comprising administering to a mammal in need thereof a pharmaceutically effective amount of the compound according to the present invention. This invention is advantageously directed to a method of delivering a prostaglandin according to the present invention to a mammalian organism in need of treatment thereof via a bisphosphonate delivery agent wherein the prostaglandin enhances the rate of bone formation and is thus effective in treating osteoporosis, bone fractures, and effective in enhancing the rate of successful bone grafts.

DETAILED DESCRIPTION OF THE INVENTION

The present invention relates to compounds that are effective as chemical delivery agents and compounds which are useful in the treatment and prevention of osteoporosis and calcium metabolism disorders. The compounds of the invention may also have dual activity as a bone growth promoter and as a bone resorption inhibitor. The compounds of the present invention are described by the following chemical formulas:

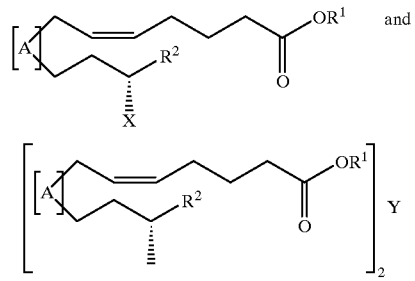

and mixtures thereof and the pharmaceutically acceptable salts thereof, wherein:

A is a dioxygenated cycloetane moiety selected from the group consisting of:

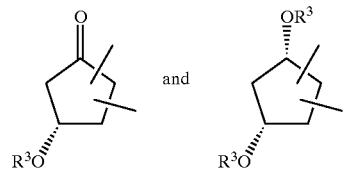

X is selected from the group consisting of:

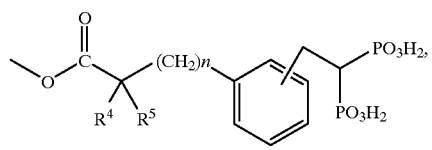

-continued

[Chemical structure: methyl ester with (CH₂)ₙ-S-(CH₂)₃-CH(PO₃H₂)₂, with R⁴, R⁵ substituents]

and

[Chemical structure: methyl ester with (CH₂)ₙ-S(O)-(CH₂)₃-CH(PO₃H₂)₂, with R⁴, R⁵ substituents]

Y is selected from the group consisting, of:

[Chemical structure: bis-methyl ester linked through S-CH₂-aryl-CH₂-S with pendant CH(PO₃H₂)₂]

and

[Chemical structure: bis-methyl ester linked through S-CH₂-aryl-CH₂-S(O) with pendant CH(PO₃H₂)₂]

$R^1$ is selected from the group consisting of H, C1–C10 alkyl, and Si(CH₃)₂tBu;

$R^2$ is selected from the group consisting of H and $C_{1-10}$ alkyl;

$R^3$ is selected from the group consisting of H, tetrahydropyran, and Si(CH₃)₂tBu;

$R^4$ and $R^5$ are independently selected from the group consisting of H, C1–C10 alkyl, phenyl, benzyl, C1–C10 alkoxy, and CF₃, and n is an integer from 0 to 5.

In the present invention, compounds are preferably selected from the following formula:

[Chemical structure: cyclopentane A with CH=CH-(CH₂)₃-C(O)OR¹ and R²/X substituents]

and mixtures thereof and the pharmaceutically acceptable salts thereof, wherein:

A is a dioxygenated cyclopentane moiety selected from the group consisting of:

[Chemical structure: cyclopentanone with OR³ substituent]

and

[Chemical structure: cyclopentane diol with two OR³ substituents]

X is selected from the group consisting of:

[Chemical structure: methyl ester with (CH₂)ₙ-aryl-CH(PO₃H₂)₂]

[Chemical structure: methyl ester with (CH₂)ₙ-S-(CH₂)₃-CH(PO₃H₂)₂]

and

[Chemical structure: methyl ester with (CH₂)ₙ-S(O)-(CH₂)₃-CH(PO₃H₂)₂]

$R^1$ is selected from the group consisting of H, C1–C10alkyl, and Si(CH₃)₂tBu;

$R^2$ is selected from the group consisting of H and $C_{1-10}$ alkyl;

$R^3$ is selected from the group consisting of H, THP, and Si(CH₃)₂tBu;

$R^4$ and $R^5$ are independently selected from the group consisting of H, C1–C10 alkyl, phenyl, benzyl, C1–C10 alkoxy, and CF₃, and n is an integer from 0 to 5.

In the compounds of the present invention, X is preferably selected from the group consisting of

[Chemical structure: methyl ester with (CH₂)n-S-(CH₂)₃-CH(PO₃H₂)₂]

and

[Chemical structure: methyl ester with (CH₂)n-S(O)-(CH₂)₃-CH(PO₃H₂)₂]

More preferably, M is

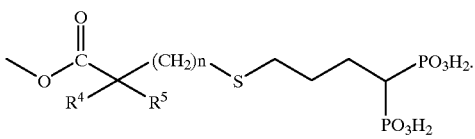

In the compounds of the present invention, A is preferably

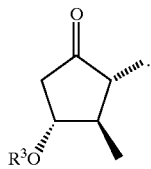

In the compounds of the present invention, n is preferably zero.

In the compounds of the present invention, $R^1$, $R^3$, $R^4$ and $R^4$ are each preferably H.

In the compounds of the present invention, $R^2$ is preferably n-$C_5H_{11}$.

Nonlimiting examples of compounds of the present invention are: $PGE_2$ bisphosphonate conjugates, $PGE_2$ bisphosphonate sulfoxide conjugates and Bis-($PGE_2$)-bisphosphonate conjugates.

An embodiment of the invention is a method of inhibiting bone resorption in a mammal comprising administering to a mammal in need thereof a therapeutically effective amount of the compounds of the present invention.

A nonlimiting class of the embodiment is wherein said mammal is a human.

A second embodiment of the invention is a method for treating or reducing the risk of contracting a disease state or condition associated with bone resorption comprising administering to said mammal a therapeutically effective amount of the compounds of the present invention.

A nonlimiting class of the second embodiment is wherein said mammal is a human.

A nonlimiting subclass of the class of the second embodiment is wherein said disease state or condition is selected from the group consisting of osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

A third embodiment of the invention is a method of increasing the bone fracture healing rate in a mammal comprising administering to a mammal in need thereof a therapeutically effective amount of the compounds of the present invention.

A fourth embodiment of the invention is a method for enhancing the rate of successful bone grafts in a mammal comprising administering to a mammal in need thereof a therapeutically effective amount of the compounds of the present invention.

A fifth embodiment of the invention is a method for enhancing the rate of bone formation in a mammal comprising administering to a mammal in need thereof a therapeutically effective amount of the compounds of the present invention.

Prostaglandins of the PGD, $PGE_2$, $PGE_1$ and $PGF_{2a}$ class or other suitable prostaglandin with a carboxylic acid moiety at the 1 position and a hydroxyl group at the 15 position of the PG moiety may be reacted with an amino bisphosphonate such as ABP or its salts to form the compounds claimed in the instant invention. Any known bisphosphonate which has an amine functionality capable of coupling to a prostaglandin and which targets in vivo to bone may be used in this invention as a chemical delivery agent whether or not that particular bisphosphonate has bone resorption inhibiting activity.

The claimed compounds may be used in treating a variety of calcium metabolism disorders including:

(1) A method of treating or preventing osteoporosis by administering a pharmaceutically effective amount of compounds within the scope of the present invention.

(2) A method of increasing the bone fracture healing rate in a mammal exhibiting a bone fracture by systemically administering a pharmaceutically effective amount of compounds within the scope of the present invention.

(3) A method for enhancing the rate of successful bone grafts comprising administering to a mammal in need thereof a pharmaceutically effective amount compounds within the scope of the present invention.

(4) A method of treating periodontal disease or alveolar bone loss by administering a pharmaceutically effective amount of compounds within the scope of the present invention.

The bisphosphonates which may be used in the present invention include any aminoalkyl bisphosphonate such as alendronate, pamidronate (3-amino-1-hydroxypropylidene) bisphosphonic acid disdoium salt, pamidronic acid, risedronate (1-hydroxy-2-(3-pyridinyl)ethylidene) bisphosphonate, YM 175 [(cycloheptylamino)methylenebisphosphonic acid], piridronate, aminohexanebisphosphonate, tiludronate, BM-210955, CGP-42446, and EB-1053.

The novel method of delivering prostaglandins via the compounds disclosed and claimed in the instant invention to the site at which bone growth stimulation is desired requires, in order to enhance bone formation, daily delivery of about 0.0001 to about 1 mg of prostaglandin. The preferred range to achieve increased bone volume is between 0.1 microgram and 0.3 microgram per day of $PGE_2$. Cortical bone mass may also be increased using a $PGE_2$ equivalent dose of 0.3 microgram per day. The quantities delivered via the novel method claimed in the instant invention are clearly an improvement over the 3 mg/day necessary to achieve an equivalent bone formation effect when a prostaglandin is administered systemically.

The prostaglandins which may be used in the present invention include but are not limited to $PGE_2$, $PGE_1$, and their analogues and $PGF_2$alpha and its analogues. The invention also encompasses pharmaceutical compositions containing compounds within the scope of the invention as active ingredients and those fillers or other inactive ingredients which those skilled in the art recognize as important for the safe and effective delivery of the claimed composition to a patient or patients in need thereof.

Protecting groups utilized in the synthesis of compounds within the scope of the present invention include, but are not limited to, THP. Other well known alcohol protecting groups include benzyl halides, MEM, and alkylcarbonylhalides.

The following examples demonstrate both the syntheses of some of the compounds within the scope of the present invention and also demonstrate the specific ability of the claimed compounds to target to bone cells in vitro and in vivo. The examples show that the uptake of $^{14}C/^3H$ dual labeled compound shown below and claimed in the instant invention to human bone powder in vitro occurs within one minute in fetal bovein serum. About 77% of the $^{14}$C moiety and 53% of the $^3$H moiety of the compound shown below is taken up by the bone powder. Disassociation of the PG moiety from the bisphosphonate from human bone powder in fetal bovien serum occurs at a rate of approximately 5%/day at 37° C. Both radiolabel experiments and radioimmunoassay experiments confirm release of the prostaglandin from the bisphosphonate at the bone cell site.

In vivo experiments also demonstrate that compounds disclosed and claimed in the present invention are delivered to bone. For example, uptake of the labeled compound shown below into rat tibiae and femora after a single dose was administered intravaneously was demonstrated. The animals used in this experiment were sacrificed at 24 hours, 14 and 28 days after the compounds claimed in the instant invention were administered. The radioactivity of the $^{14}$C and $^3$H was measured after incineration of the long bones to determine the percentage of compound retained in the bone. The examples further show that compounds within the scope of the present invention significantly inhibit the production of lysylpuridinolines (LP) over certain time periods. High LP levels are normally associated with the breakdown of bone collagen.

The compounds claimed in the instant invention are therefore useful in the treatment of diseases or conditions in which bone loss or degradation or fracture has occured. The compounds claimed in the instant invention, as the specification discloses and as the schemes and examples demonstrate, administered in pure form or in a pharmaceutical composition are effective in delivering a bone healing or bone growth enhancing amount of a prostaglandin to a patient or organism in need of such treatment. In addition, the compounds may also be used as bone growth enhancers and bone resorption inhibitors if the particular bisphosphonate used has bone resorption inhibiting activity or if the entire compound prior to hydrolysis has bone resorption inhibiting activity.

The term "pharmaceutically acceptable salts" shall mean non-toxic salts of the compounds of this invention which are generally prepared by reacting the free based with a suitable organic or inorganic acid. Representative slats include the following salts: acetate, benzenesulfonate, benzoate, bicarbonate, bisulsfate, bitartrate, borate, bromide, calcium edtate, camsylate, carbonate, chloride clavulanage, citrate, dihydrochloride, edetate, edisylate, estolate, esylate, fumarate, glucoheptanate, gluconate, glutamate, glycollylarsanilate, hexylresorcinate, hydrbamine, hydrobromide, hydrochloride, hydroxynapthoate, iodide, isothionate, lactate, lactobionate, laurate, malate, laeate, madelate, mesylate, methylbromide, methylnitrate, methylsulfate, mucate, napsylate, nitrate, oleate, oxalate, pamaote, palmitate, pantothenate, phosphoate/diphosphate, polygalactouronate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a physician or veterinarian.

The term "aryl" shall mean a mono- or polycyclic system composed of 5- and/or 6-membered aromatic rings containing 0, 1, 2, 3, or 4 heteroatoms chosen from N, O, or S and either unsubstituted or substituted independently with $R^1$ to $R^{12}$. The term "alkyl" shall mean C1–C30 straight or branched alkane, alkene, or alkyne. the term "alkoxy" shall be taken to include an alkyl portion where alkyl is as defined above.

The terms "arylalkyl" and "alkylaryl" shall be taken to include an alkyl portion where alkyl is a defined above and to include an aryl portion where aryl is as defined above. The CO-n or C1-n designation where n may be an interger form 1–10 or 2–10 respectively refers to the alkyl component of the arylalkyl or alkylaryl unit.

The term "halogen" shall include fluorine, chlorine, iodine, and bromine.

The term "oxy" shall mean an oxygen (O) atom. The term "oxo" refers to a bivalent oxygen atom (=O). The term "thio" shall mean a sulfur (S) atom.

The term substituted phenyl shall mean a phenyl substituted with a halogen, alkyl, or $CF_3$.

The site at which bone growth stimulation is desired is meant both the area adjacent to a section of bone or group of bones in need of treatment in a human or other organism in need thereof or a region inside the bone, including the site of a fracture or opening which occurs naturally or is intentionally made in the bone or group of bones.

The term "broken bone" means all types of broken bones such as green stick fractures, compound fractures, lateral fractures, pathologic fractures resulting from invasive tumors, compression fractures and fractures that require surgical procedures for realignment of bones.

The term "bisphosphonate delivery agent" as recited herein means any known bisphosphonate that effectively targets bone and is capable of reacting with a prostaglandin as recited herein. The bisphosphonate delivery agents include all commercially known bisphosphonates used in the treatment of osteoporosis and further includes those specifically recited in this disclosure. The above term also includes those bisphosphonates that target bone and are safe and effective whether or not the bisphosphonate is useful in the treatment of osteoporosis.

In the schemes and examples below, various reagent symbols have the following meanings:

| | |
|---|---|
| BOC(Boc): | t-butyloxycarbonyl. |
| THP: | tetrahydropyran. |
| Pd—C: | Palladium on activated carbon catalyst. |
| DMF: | Dimethylformamide. |
| DMSO: | Dimethylsulfoxide. |
| DCC: | 1,3-Dicyclohexylcarbodiimide. |
| CBZ(CBz): | Carbobenzyloxy or benzyloxycarbonyl. |
| $CH_2Cl_2$: | Methylene chloride. |
| $CHCl_3$: | chloroform. |
| $CH_3CN$: | acetonitrile. |
| EtOH: | ethanol. |
| CDI: | Carbonyldiimidazole. |
| MeOH: | methanol. |
| EtOAc: | ethylacetate. |
| HOAc: | acetic acid. |
| EDC: | 1-(3-Dimethylaminopropyl)-3-ethylcarbodiimide. |
| LDA: | Lithium diisopropylamide. |
| THF: | tetrahydrofuran. |

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-osteoporosis agent or as a fracture healing agent.

Compounds of the invention may be administered to patients where prevention of osteoporosis or other bone related disorder is desired.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents, electrolytes, and coloring agents can also be incorporated into the mixture. The present composition may be administered in the form of tablets, caplets, gelcaps, capsules, elixirs, syrups, or suspensions. For oral administration, the active ingredients may be admixed with a pharmaceutically acceptable diluent such as lactose, sucrose, cellulose, dicalcium phosphate, calcium sulfate, mannitol, and, in a liquid composition, ethyl alcohol. Acceptable emulsifying or suspending agents such as PVP, gelatin, natural sugars, corn sweeteners, natural and synthetic gums such as acacia, sodium alginate, guar gum, agar, bentonite, carboxymethylcellulose sodium, polyethylene glycol and waxes, may also be admixed with the active components. Where necessary, lubricants such as magnesium stearic acid talc or magnesium stearate, and disintegrators or superdisintegrators such as starch, sodium starch glycolate or cross-linked PVP may also be included. Electrolytes such as dicalcium phosphate, sodium benzoate, sodium acetate and sodium chloride may also be used. Disintegrators also include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include poly-vinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-osteoporosis drugs to achieve synergystic effects in the treatment of various pathologies. They may also be combined with known bisphosphonates or other suitable compounds which are used to treat osteoporosis, bone-related disorders, or bone fractures.

The novel compounds of the present invention are prepared according to the procedure of the schemes and examples described in this specification, using appropriate materials and are further exemplified by the following specific examples. The most preferred compounds of the invention are any or all of those specifically set forth in these examples and schemes. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

All reagents and dry solvents are obtained from commercial sources and used without further purification. ([5,6,8, 11,12,14,15-$^3$H(N)]-PGE$_2$ is purchased from New England Nuclear and 3-[$^{13}$C]-3-amino-1-hydroxypropane-1,1-diphosphonate($^{14}$C-alendronate)($^{14}$C-ABP) is synthesized by Merck Research Laboratories, Rahway, N.J.). All reactions were carried out under a positive pressure of nitrogen. Flash chromatography is performed on silica-gel (Merck, 230–400 mesh). Bond Elute C18 pak cartridges are obtained from Varian Inc. and washed with CH$_3$CN, methanol and water before use. $^1$H and $^{13}$C NMR spectra are recorded on a Bruker ARX-400 or AMX-300 instrument. Infrared spectra are recorded on a Perkin-Elmer 681 spectrometer. Melting points are taken on a Mettler FP61 apparatus and are uncorrected. Low resolution mass spectra and elemental analyses are obtained from Oneida Research Services. High resolution mass spectra were obtained at the Biomedical Mass Spectrometry Unit, McGill University using a ZAB 2F HS instrument.

EXAMPLE 1

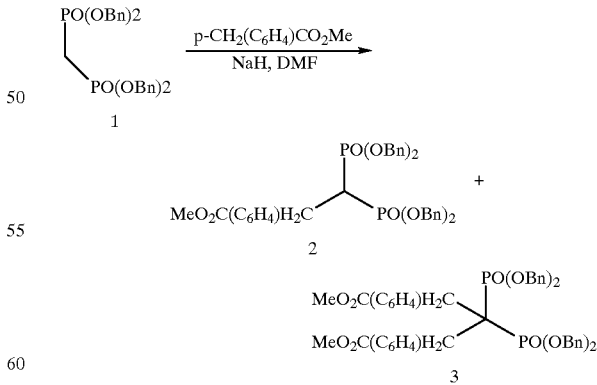

Tribenzyl orthoformate

Benzyl alcohol (390 mL, 3.6 mol) is added to a solution of triethyl orthoformate (150 mL), 0.9 mol) in benzene (350 mL) at room temperature. Trifluoroacetic acid (6.8 mL, 0.09 mol) is then added at room temperature and the mixture is slowly distrilled under reduced pressure (35° C., 20 mm Hg) until the volatiles (EtOH, C$_6$H$_6$, TFA) have distilled. Excess benzyl alcohol is distilled (75° C., 0.1 mm Hg) and the residue consists mainly of tribenzyl orthoformate which can be distilled (170–185° C., 0.1 mm Hg) although it can be used crude in the next step. $^1$H NMR (CDCl$_3$): δ 7.40 (15H, s), 5.50 (1H, s), 4.74 (6H, s). $^{13}$C NMR (CDCl$_3$): δ 137.8, 128.9, 128.1, 111.8, 66.5.

Tetrabenzyl methylenediphosphonate (1)

A mixture of methylenediphosphonic acid (14.8 g, 0.08 mol) and tribenzyl orthoformate (226 g, 0.68 mol) is heated to 150 ° C. for 2 hours, cooled down, diluted with ethyl acetate (125 mL) and poured onto a silica gel column (4.5 L) column. Elution with ethyl acetate gives 34.6 g (77%) of tetrabenzyl methylenediphosphonate 1 as an oil. IR (neat) 3100–2900 cm$^{-1}$. $^1$H NMR (CDCl$_3$): δ 7.29 (20H, m), 4.98 (8H, m), 2.50 (2H, t, J=24.0 Hz). $^{13}$C NMR (CDCl$_3$): δ 136.1, 128.9, 128.8, 128.2, 128.1, 68.4, 26.4 (t, J=138.4 Hz). MS (FAB, NaI) m/z (relative intensity): 537 (MH$^+$, 96), 447 (7), 181 (100). HRMS (FAB, NaI): calcd for C$_{29}$H$_{31}$P$_2$O$_6$ (MH$^+$) 537.1596; found 537.1594. Anal. calcd for C$_{29}$H$_{31}$P$_2$O$_6$: C, 64.91; H, 5.64; P, 11.55; found: C, 64.69; H, 5.85; P, 11.26.

Tetrabenzyl 2-(4-carbomethoxyphenyl)ethane-1,1-diphosphonate (2)

Sodium hydride (60%) (291 mg, 7.3 mmol) is added portionwise to a solution of tetrabenzyl methylenediphosphonate (1) (3.0 g, 5.5 mmol) in DMF (10.0 mL) at room temperature. The mixture is stirred at room temperature for 60 minutes and a solution of methyl p-bromomethylbenzoate (1.9 g, 8.4 mmol) in THF (2.0 mL) is added. The mixture is stirred at room temperature for 30 minutes and a solution of saturated ammonium chloride (15 mL), water (100 mL), and a (1:1) mixture of ether: hexanes (100 mL) are added. The separated aqueous layer is extracted with a (1:1) mixture of ether: hexanes (3×100 mL) and the combined organic layers are washed (brine), dried (MgSO$_4$ anh.), filtered and evaporated. Flash-chromatography (EtOAc: hexanes (1:1)) of the residue gives monoalkylated product 2 (1.8 g, 47%) along with dialkylated product 3 (670 mg, 14%). Spectral data for compounds 2 and 3 are given below.

2: IR (neat) 3100–2890, 1720 cm$^{-1}$. $^1$H NMR (CDCl$_3$): δ 7.80 (2H, d, J=7.0 Hz), 7.33 (20H, m), 7.10 (2H, d, J=7.0 Hz), 4.92 (8H, m), 3.88 (3H, s), 3.26 (2H, td, J=16.7, 6.4 Hz), 2.71 (1H, tt, J=24.0, 6.4 Hz). $^{13}$C NMR (CDCl$_3$): δ 166.8, 144.4, 136.0, 129.5, 128.9, 128.5, 128.4, 128.2, 128.1, 68.1 (dd, J=24.1, 6.6 Hz), 51.9, 40.8, 39.6 (t, J=132.5 Hz), 31.3 (t, J=6.2 Hz). MS (FAB, NaI) m/z (relative intensity): 685 (42), 301 (10), 181 (100). HRMS (FAB, NaI): calcd for C$_{38}$H$_{39}$P$_2$O$_8$ (MH$^+$) 685.2120; found 685.2122.

3: IR (neat) 3100–2890, 1725 cm$^{-1}$. $^1$H NMR (CDCl$_3$): δ 7.79 (4H, d, J=7.0 Hz), 7.40 (2H, d, J=7.0 Hz), 7.33 (20H, m), 4.85 (8H, m), 3.86 (6H, s), 3.40 (4H, t, J=16.0 Hz). $^{13}$C NMR (CDCl$_3$): δ 168.9, 141.5, 135.9, 131.7, 128.8, 128.7, 128.5, 128.4, 128.2, 68.2 (t, J=2.9 Hz), 51.9, 49.3 (t, J=130.9 Hz), 38.3 (t, J=6.2 Hz). MS (FAB, NaI) m/z (relative intensity): 833 (23), 603 (16), 449 (11), 181 (100). HRMS (FAB, NaI): calcd for C$_{47}$H$_{47}$P$_2$O$_{10}$ (MH$^+$) 833.2645; found 833.2642.

EXAMPLE 2

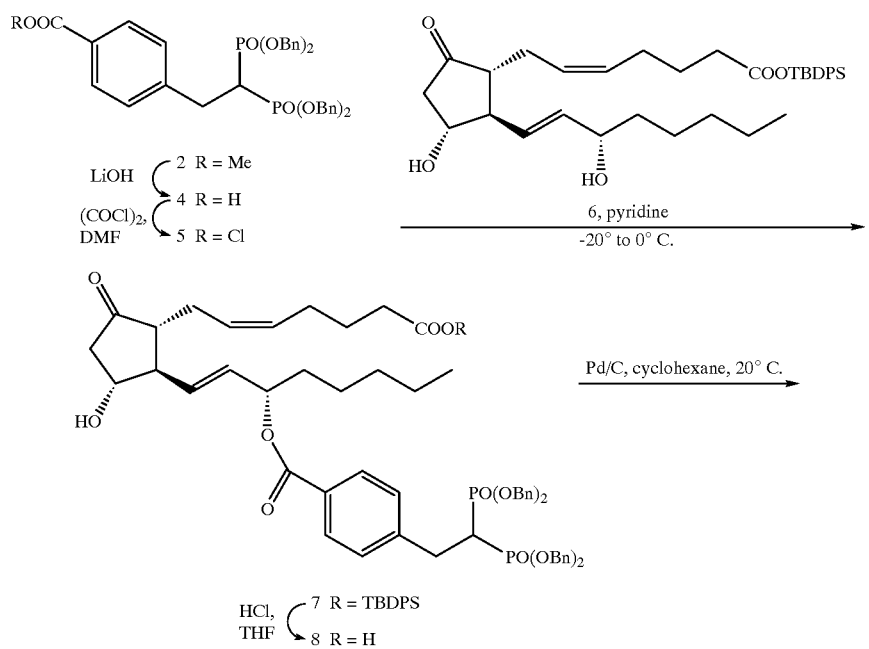

-continued

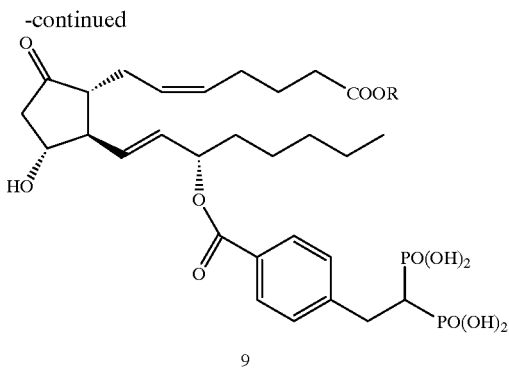

9

Tetrabenzyl 2-(4-carboxyphenyl)ethane-1,1-diphosphonate (4)

A solution of lithium hydroxide (84 mg, 2.0 mmol) in water (1.0 mL) is added to a solution of methyl ester 2 (455 mg, 0.6 mmol) in 1,4-dioxane (1.0 mL) at room temperature. The mixture is stirred at room temperature for 5 hours and a 1N solution of HCl (10 mL) is added. Dioxane is evaporated under reduced pressure and the mixture is diluted with EtOAc (20 mL). The separated aqueous layer is extracted with EtOAc (3×50 mL) and the combined organic layers are washed (brine), dried (MgSO$_4$ anh.), filtered and evaporated. Flash-chromatography (HOAc:EtOH:EtOAc (0.1:1:9)) of the residue gives carboxylic acid 4 (210 mg, 48%). $^1$H NMR (CDCl$_3$): δ 9.65 (1H, br. s), 7.98 (2H, d, J=8.1 Hz), 7.26 (20H, s), 7.13 (2H, d, J=8.1 Hz), 4.95 (8H, m), 3.31 (2H, td, J=16.7, 6.4 Hz), 2.82 (1H, tt, J=24.0, 6.4 Hz). $^{13}$C NMR (CDCl$_3$): δ 170.0, 144.6 (t, J=7.6 Hz), 135.9, 135.8, 130.1, 129.0, 128.6, 128.5, 128.4, 128.3, 128.2, 128.1, 68.3 (dd, J=19.6, 6.5 Hz), 39.4 (t, J=133.2 Hz), 31.2 (br. s).

PGE$_2$-TBDPS ester bisphosphonate conjugate (7a)

Freshly distilled oxalyl chloride (1.5 equivalent) is added to a solution of the acid 4 (177 ng, 0.264 mmol) and DMF (10 μl, 0.132 mmol) in dichloromethane (1 ml) at 0° C. After stirring 10 min. the volatiles are evaporated under high vacuum and the residue acid chloride 5 used directly. IR (neat): 1770, 1740 cm$^{-1}$. 5 is dissolved in dichloromethane (100 μl), cooled to −20° C. and pyridine 50 μl is added followed by PGE$_2$-TBDPS in pyridine (350 μl) and dichloromethane (100 μl). After stirring 10 min. at −10° C. and 0.5 h at 0° C. A solution of saturated ammonium chloride is added and the mixture is extracted with EtOAc acetate (3×5 ml). The organic extracts are washed with brine, dried over magnesium sulfate and evaporated to dryness. The residue is purified by HPLC (ZORBAX, 21-5×25 cm, 20 ml/min EtOAc: hexane, (80/20) as eluant). The first fraction corresponds to the C-11 regioisomer 7b (66.4 mg; 18%). The second fraction is the desired C-15 regioisomer 7a (156.4 mg, 42%). Ethyl acetate elution provides the bis-acylated product (20 mg) and recovers PGE$_2$-TBDPS (55.3 mg, 31.4%).

C-15 isomer 7b: IR (neat) 3400, 3060–2860, 1740–1720 cm$^{-1}$. $^1$H NMR (CDCl$_3$): δ 7.78 (2H, d, J=8.2 Hz), 7.66, 7.64 (4H, 2d, J=7.9 Hz), 7.43–7.18 (26H, m), 7.11 (2H, d, J=8.2 Hz), 5.67, 5.39 (4H, 2m), 5.28 (1H, m), 4.93 (8H, m), 4.05 (1H, m), 3.28 (2H, td, J=16.6, 6.4 Hz), 2.72 (1H, tt, J=24.0, 6.4 Hz), 2.71 (1H, m), 2.44 (2H, t, J=7.5 Hz), 2.41–1.22 (19H, m), 1.09 (9H, s), 0.86 (3H, m). $^1$H NMR (CD$_3$COCD$_3$): δ 7.85 (2H, d, J=8.3 Hz), 7.73, 7.72 (4H, 2d, J=7.7 Hz), 7.48–7.26 (28H, m), 5.87 and 5.78 (2H, 2dd, J=15.5, 7.8 Hz and J=15.5, 6.5 Hz respectively), 5.52, 5.40 (3H, m), 5.03 (8H, m), 4.31 (1H, d, J=5.1 Hz), 4.16 (1H, m), 3.33 (2H, td, J=16.4, 6.6 Hz), 3.05 (1H, tt, J=23.7, 6.6 Hz), 2.67–1.20 (19H, m), 1.10 (9H, s), 0.87 (3H, m). $^{13}$C NMR (CD$_3$COCD$_3$): δ 214.3, 173.0, 165.9, 145.7 (t, J=7.8 Hz), 137.5 (dd, J=9.0, 6.9 Hz), 136.0, 130.1, 129.2, 75.5, 72.4, 68.5 (m), 54.8, 53.9, 39.8 (t, J=131.1 Hz), 47.5, 35.9, 35.4, 33.9, 32.3, 27.3, 25.8, 25.7, 23.2, 19.6, 14.3. MS (FAB, NaI) m/z (relative intensity): 1265 (M+Na$^+$, 24), 1243 (13), 1192 (17), 819 (13), 761 (16), 671 (100), 581 (62). HRMS (FAB, NaI): calcd for C$_{73}$H$_{85}$P$_2$SiO$_{12}$ (MH$^+$) 1243.5286; found 1243.5287. C-11 isomer 7b: IR (neat) 3400, 3060–2860, 1740–1720 cm$^{-1}$. $^1$H NMR (CDCl$_3$): δ 7.75 (2H, d, J=8.3 Hz), 7.64 (4H, m), 7.46–7.18 (26H, m), 7.11 (2H, d, J=8.3 Hz), 5.62–5.21 (5H, 4m), 5.28 (1H, m), 4.93 (8H, m), 4.06 (1H, d, J=6.6 Hz), 4.00 (1H, m), 3.27 (2H, td, J=16.7, 6.5 Hz), 3.00 (1H, dd, J=18.3, 6.8 Hz), 2.79–1.11 (19H, m), 1.09 (9H, s), 0.81 (3H, br. t, J=6.7 Hz).

PGE$_2$ bisphosphonate ester conjugate (8)

To a solution of PGE$_2$-TBDPS ester conjugate 7a (145 mg, 0.117 mmol) in THF (4 mL) and 0.2 N HCl (1 mL) is stirred at room temperature for 4 h and diluted with brine, extracted with EtOAc (4×10 mL). The extracts are combined, concentrated in vacuo and the residue is purified by circular chromatography (EtOAc/hexane=80/20) to furnish the corresponding acid (110 mg, 94%). 17: IR (neat) 3680–3200, 3000–2840, 1740 cm$^{-1}$. $^1$H NMR (CDCl$_3$): δ 7.79 (2H, d, J=8.0 Hz), 7.25 (20H, m), 7.13 (2H, d, J=8.0 Hz), 5.68 (2H, 2m), 5.37 (3H, m), 4.92 (8H, m), 4.07 (1H, m), 3.26 (2H, td, J=16.6, 6.2 Hz), 2.84 (1H, tt, J=24.0, 6.2 Hz), 2.68 (1H, br. dd, J=18.4, 7.4 Hz), 2.41–1.22 (19H, m), 1.09 (9H, s), 0.86 (3H, m). $^{13}$C NMR (CDCl$_3$): δ 214.8, 176.7, 165.2, 144.4 (t, J=7.6 Hz), 135.8 (dd, J=9.0, 6.9 Hz), 131.5, 129.3, 128.6, 128.5, 128.2, 74.9, 72.0, 68.3, 54.5, 53.2, 39.2 (t, J=132.9 Hz), 46.2, 34.5, 33.4, 31.6, 31.1, 26.6, 25.1, 24.9, 24.6, 22.5, 14.0. MS (FAB, NaI) m/z (relative intensity): 1027 (M+Na$^+$, 31), 671 (100). HRMS (FAB, NaI): calcd for C$_{57}$H$_{67}$P$_2$O$_{12}$ (MH$^+$): 1005.4108; found: 1005.4106.

PGE$_2$ bisphosphonate conjugate (9)

In a 3 mL boronsilicate test tube a solution of the acid 8 (36 mg, 0.036 mmol) in EtOH (420 mL) and EtOAc (80 mL) under nitrogen is immersed in a 20° C. water bath. To the solution is added Pd/C (5% Pd content, 5.7 mg, 0.036 mmol) followed by 1,4-cyclohexadiene (136 mL, 1.44 mmoL) and the resultant mixture is stirred at room temperature for 4.5 h and transferred to a 1.5 mL plastic Eppendorf vial and centrifuged. The supernatant is removed out and the residue rinsed twice with ethanol (1 mL). The supernatants are combined, neutralized with 0.5 N ammonium acete (144 mL, 0.072 mmol) and concentrated. The crude product (~90% pure by $^1$H NMR) can be purified in two ways: 1) by C18 mini-columns (6 mL Varian Bond Elute) using water (5 mL), 30% MeOH/water (5 mL), 60% MeOH/water (5 mL) and MeOH (5 mL). The desired product is eluted with the 30% MeOH/water fraction. The fraction is lyophilized to afford the compound 9 (21 mg, 76%); as a light yellow fluffy powder. 2) by HPLC using Waters PrepPak μbondapak® C18 column (25×100 mm, 10 mL/min, gradient composition: 0.5 N $NH_4OAc/CH_3CN$=90/10 to 70/30 in 10 min and 70/30 for 10 min, UV detection: 254 nm). The fractions thus obtained are lyophilized to give the desired product, 9. $^1H$ NMR ($D_2O$): δ 7.82 (2H, d, J=7.9 Hz), 7.37 (2H, d, J=7.9 Hz), 5.65 (2H, m), 5.37 (2H, m), 5.19 (1H, m), 4.05 (1H, m), 3.03 (2H, m), 2.65 (1H, dd, J=18.8, 7.5 Hz), 2.42–1.16 (21H, m), 0.71 (3H, m). $^{13}C$ NMR ($D_2O$): δ 222.1, 180.0, 169.5, 133.9, 133.0, 130.4, 130.3, 77.2, 72.1, 53.2, 42.1, 40.4, 35.1, 34.6, 34.5, 32.4, 32.1, 31.8, 25.2, 25.1, 22.9, 14.3. MS (FAB, NaI) m/z (relative intensity): 667 (M+$Na_+$, 4), 645 (2), 399 (4), 311 (11), 293 (14), 177 (60), 136 (100). HRMS (FAB, NaI): calcd for $C_{29}H_{43}P_2O_{12}$ ($MH^+$): 645.2231; found: 645.2230.

EXAMPLE 3

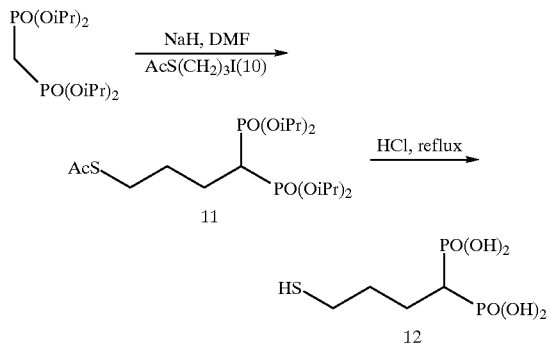

3-acetylthiopropyliodide (10)

To a solution of 1,3-diiodopropane (10 g, 33.8 mmol) in 10 ml of anhydrous DMF at 0° C. under nitrogen is added, via a cannula over 15 min, a solution of potassium thioacetate (1.3 g, 11.3 mmol) in 5 ml of DMF and the mixture is stirred at 0° C. for 0.5 h, quenched with water (20 ml) and extracted with ether (3×20 ml). The extracts are combined, washed with brine and dried over $MgSO_4$, filtered and concentrated. The residue is purified by flash chromatography (silica gel, EtOAc:hexane/5:95–10:90) to yield iodide 10 (2.5 g, 90%) as a light yellow oil. IR (neat) 2960, 2920, 1689, 1418, 1350, 1210, 1130 $cm^{-1}$; $^1H$ NMR ($CDCl_3$) δ 2.00 (2H, m), 2.26 (3H, s), 2.87 (2H, t, J=7 Hz), 3.13 (2H, t, J=6.9 Hz); $^{13}C$ NMR ($CDCl_3$) δ 4.35, 29.70, 30.63, 32.97, 195.09.

Tetraisopropyl 4-acetylthiobutane-1,1-diphosphonate (11)

To a solution of tetraisopropyl methylenediphosphonate (9.35 g, 27 mmol) in anhydrous DMF (30 ml) is added NaH (0.96 g, 32 mmol) portionwise and the resulting suspension is stirred at room temperature for 1 h. To the above solution is then introduced dropwise a solution of iodide 10 in DMF (7 ml) and the mixture is stirred at room temperature for 2 h, quenched with saturated aqueous ammonium chloride and extracted with EtOAc (3×60 ml). The extracts are combined, washed with brine and dried over $Na_2SO_4$, filtered and concentrated in vacuo. The residue is subjected to Kughrör distillation to remove the unreacted starting material. The residue of the distillation is purified by flash chromatography (silica gel, EtOH: $CH_2Cl_2$/0:100–3:97) to furnish bisphosphonate 11 (4.5 g, 36%) as a colorless oil. IR (neat) 2980, 2930, 2875, 1692, 1381, 1370, 1248 $cm^{-1}$; $^1H$ NMR ($CDCl_3$): δ 1.27 (24H, m), 1.73–1.92 (4H, m), 2.06 (1H, tt, J=24.1, 5.8 Hz), 2.23 (3H, s), 2.80 (2H, t, J=7 Hz), 4.70 (4H, m); $^{13}C$ NMR ($CDCl_3$): δ 23.06, 23.11, 23.16, 23.42, 24.30 (t, J=5 Hz), 27.85, 28.06 (t, J=6.6 Hz), 29.71, 37.18 (t, J=135 Hz), 70.10 (d, J=6.9 Hz), 70.25 (d, J=7 Hz), 194.11; MS (FAB) m/z (relative intensity) 461 ($MH^+$, 46), 251 (100); HRMS calcd for $C_{18}H_{39}O_7P_2S$ ($MH^+$) 461.1891, found 461.1892.

4-mercaptobutane-1,1-diphosphonic acid (12)

A solution of bisphosphonate 11 (2.07 g, 4.5 mmol) in 40 ml of 6N HCl is heated to reflux under nitrogen for 6 h and cooled to room temperature. The solution is concentrated under high vacuum to afford 12 (1.1 g, 98%) as a yellowish oil. $^1H$ NMR ($D_2O$, 400 MHz) δ 1.54–1.78 (4H, m), 2.08 (1H, tt, J=23.6, 5.9 Hz), 2.31 (2H, t, J=6.7 Hz); $^{13}C$ NMR ($D_2O$, 100 MHz) δ 24.13, 24.63 (t, J=4.5 Hz), 33.46 (t, J=6.6 Hz), 37.75 (t, J=128 Hz); MS (FAB) m/z (relative intensity) 251 ($MH^+$, 47), 217 (39), 136 (100); HRMS calcd for $C_4H_{13}O_6P_2S$ ($MH^+$) 250.9908, found 250.9908.

EXAMPLE 4

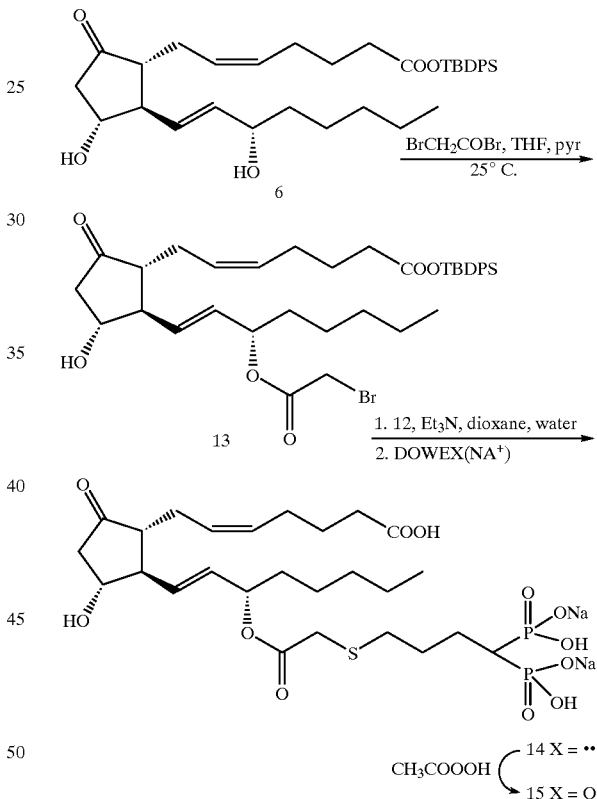

$PGE_2$-t-butyl-diphenylsilyl ester ($PGE_2TBDPS$) (6)

To a solution of $PGE_2$ (352.5 mg, 1 mmol) in $CH_2Cl_2$ (5 ml) at 0° C. is added t-butyldiphenylsilylchloride (275 μl, 1.1 mmol) and triethylamine (278 μl, 2.0 mmol) consecutively via microsyringe. The mixture is stirred at 0° C. for 2 h, then the solvent is evaporated and the residue purified by flash chromatography on silica gel eluting with ethyl acetate to provide $PGE_2$-TBDPS ester (6) 592 mg, 100%) $^1H$ NMR ($CDCl_3$): δ 7.65, 7.37 (10H, m), 5.59 (1H, dd, J=15, 7 Hz), 5.48 (1H, dd, J=15, 8 Hz), 5.38 (1H, m), 5.29 (1H, m), 4.05–3.97 (2H, m), 2.68 (1H, dd, J=15, 7 Hz), 2.44 (2H, dd, J=7, 7 Hz), 2.38–2.28 (6H, m), 2.14 (1H, dd, J=17, 9 Hz), 2.05 (3H, m), 1.70 (2H, m), 1.56–1.40 (2H, m), 1.35–1.24 (5H, m), 1.08 (9H, s), 0.86 (3H, t, J=7 Hz).

A sample of [5,6,8,11,12,14,15-³H(N)]-PGE₂-TBDPS ester is prepared by diluting [5,6,8,11,12,14,15-³H(N)]-PGE₂ (1 mCi, 100–200 Ci/mmol) into 100 mg PGE₂ to provide a final specific activity of 3.53 mCi/mmol. The PGE₂ is converted to [³H]-PGE₂-TBDPS ester (12) as above in 89% yield.

15-bromoacetyl PGE₂-TBDPS ester (13)

To a solution of PGE₂-TBDPS (3.3 g, 5.58 mmol) in anhydrous THF (9 ml) at −25° C. is added pyridine (0.54 ml, 6.7 mmol) and bromoacetylbromide (0.54 ml, 6.14 mmol) and the suspension is stirred 10 min at −25° C. to −20° C. The mixture is quenched with saturated aqueous ammonium chloride, warmed to room temperature and extracted with EtOAc. The organic layer is washed with brine, dried over Na₂SO₄ and concentrated in vacuo. The crude product is purified by flash chromatography (silica gel, EtOAc:hexane/10:90–40:60) to yield the desired compound 13 (1.93 g, 49%) as a colorless oil. IR (neat) 3460, 2950, 2928, 2855, 1725, 1460, 1424, 1270 cm⁻¹; ¹H NMR (CDCl₃): δ 0.86 (3H, t, J=6.7 Hz), 1.08 (9H, s), 1.22–1.35 (6H, m), 1.52–1.77 (4H, m), 1.88 (1H, b), 2.04–2.12 (3H, m), 2.17 (1H, dd, J=18.5, 9.4 Hz), 2.31 (1H, m), 2.35–2.50 (2H, m), 2.44 (2H, dd, J=7.7, 7.3 Hz), 2.71 (1H, ddd, J=18.4, 7.3, 1 Hz), 3.77 (2H, s), 4.07 (1H, ddd, J=9.3, 9.3, 8.5 Hz), 5.21 (1H, d, J=6.9 Hz), 5.25–5.44 (2H, m), 5.55 (1H, dd, J=15.4, 7.1 Hz), 5.66 (1H, dd, J=15.4, 8.3 Hz), 7.34–7.47 (6H, m), 7.65 (4H, m); ¹³C NMR (CDCl₃): δ 13.99, 19.16, 22.50, 24.75, 24.87, 25.18, 26.30, 26.68, 26.96, 31.42, 34.25, 35.50, 46.18, 53.25, 54.35, 71.90, 76.90, 126.45, 127.73, 130.07, 131.08, 131.33, 131.95, 133.87, 135.32, 166.82, 172.76, 213.92; MS (APCI) m/z (relative intensity) 730 (⁸¹Br)([M+NH₄]⁺, 15), 477 (63), 149 (100); MS (FAB) m/z (relative intensity) 711 (MH⁺, 1), 135 (100); HRMS calcd for C₃₈H₅₂O₆SiBr (MH⁺) 711.2716, found 711.2715.

PGE₂ bisphosphonate conjugate (14)

To a solution of bromide 13 (4.39 g, 6.16 mmol) in dioxane (50 ml) at room temperature and under nitrogen is added dropwise via a cannula a solution of thiol 12 (2.23 g, 8.92 mmol) and triethylamine (4.95 ml, 35.68 mmol) in water (20 ml) and the clear solution is stirred at room temperature for 2 h and concentrated. The residue is partitioned between EtOAc and water. The aqueous layer is washed twice with EtOAc and concentrated. The residue is purified by flash chromatography (silica gel C-18, MeOH:water/0:100–60:40). The desired product comes out in the 30% MeOH/water fractions which are filtered on a cation exchange (DOWEX 50 Na⁺ form, 35 g). The filtrate is lyophilizated to give the desired conjugate 14 (2.8 g, 66%) as a white sticky solid. ¹H NMR (D₂O): δ 0.70 (3H, m), 1.16 (6H, m), 1.40–1.60 (4H, m), 1.67–1.80 (5H, m), 1.88 (2H, m), 2.01 (2H, dd, J=8, 7.4 Hz), 2.08 (1H, dd, J=18.7,9.6 Hz), 2.22 (3H, m), 2.35 (1H, m), 2.51 (2H, m), 2.66 (1H, dd, J=18, 7.3 Hz), 3.26 (2H, s), 4.03 (1H, m), 5.10–5.20 (2H, m), 5.37 (1H, m), 5.52 (1H, dd, J=15.4, 7 Hz), 5.61 (1H, dd, J=15.4, 8.3 Hz); ¹³C NMR (D₂O): δ 14.20, 22.81, 24.96, 25.25, 25.63 (t, J=5 Hz), 26.59, 27.56, 29.47 (t, J=7.5 Hz), 31.55, 32.75, 34.29, 34.35, 37.78, 39.60 (t, J=116 Hz), 46.93, 53.33, 55.11, 71.87, 77.92, 126.84, 132.25, 132.92, 134.54, 173.33, 183.81, 221.32; MS (FAB) m/z (relative intensity) 709 ([M+Na]⁺, 1.5), 687 ([M+H]⁺, 2.7), 665 ([M+2H−Na]⁺, 1.5), 115 (100); HRMS calcd for C₂₆H₄₂O₁₂P₂SNa₃ ([M+Na]⁺) 709.1565, found 709.1564.

PGE₂ bisphosphonate sulfoxide conjugate (15)

To a solution of conjugate 14 (10 mg, 0.0145 mmol) in 1 ml of MeOH is added at room temperature a 32% peracetic acid (3.37 μl, 0.016 mmol) solution and the mixture is stirred for 10 min. Dimethyl sulfide is then added and after 5 min the solvents of the reaction are removed to give sulfoxide 15 (10.2 mg, 100%). ¹H NMR (D₂O): δ 0.69 (3H, m), 1.08–1.23 (6H, m), 1.43–1.65 (4H, m), 1.75–2.00 (7H, m), 2.07 (1H, dd, J=18.3, 9.7 Hz), 2.14–2.25 (5H, m), 2.34 (1H, m), 2.65 (1H, dd, J=19, 7.4 Hz), 2.89 (2H, m), 3.71 (1H, d, J=14.6 Hz), 3.90 (1H, d, J=14.6 Hz), 4.04 (1H, m), 5.13–5.27 (2H, m), 5.32 (1H, m), 5.51 (1H, dd, J=15.4, 6.8 Hz), 5.61 (1H, dd, J=15.4, 8.3 Hz); ¹³C NMR (D₂O): δ 14.45, 23.05, 25.18, 25.35, 25.47, 25.67, 27.22, 31.87, 34.49, 34.63, 39.47 (t, J=117 Hz), 39.59, 46.73, 51.92, 53.73, 55.12, 55.97, 71.77, 78.68, 127.47, 131.92, 132.00, 135.83, 167.19, 179.20, 179.38; MS (FAB) m/z (relative intensity) 747 ([M−H+2Na]⁺, 3.5), 725 ([M+Na]⁺, 4), 703 ([M+H]⁺, 3) 115 (100); HRMS calcd for C₂₆H₄₃O₁₃P₂SNa₂ (MH⁺) 703.1695, found 703.1696.

EXAMPLE 5

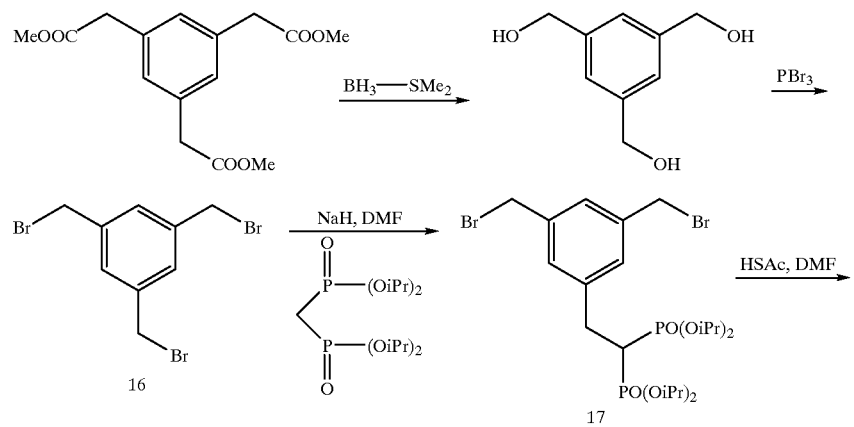

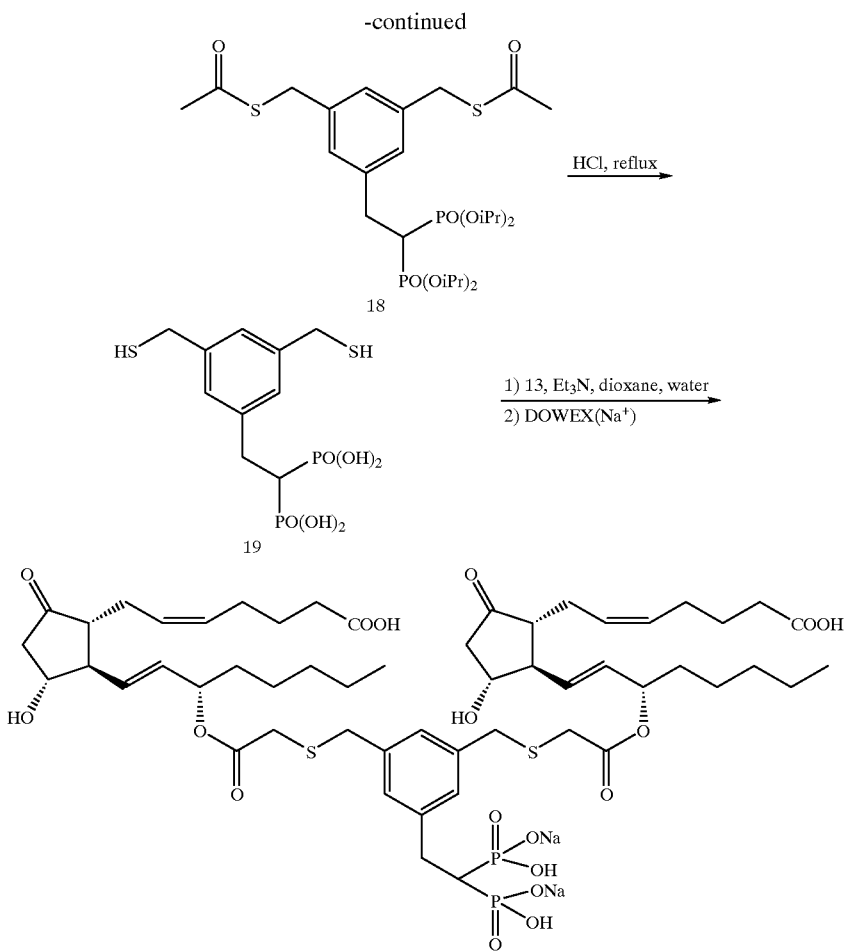

1,3,5-tris(hydroxymethyl)benzene

To a stirring solution of trimethyl 1,3,5-benzenetricarboxylate (10.45 g, 41.4 mmol) in 70 ml of anhydrous THF is added at room temperature a 10M solution of borane-methyl sulfide complex (25 ml, 248 mmol) and the solution is heated to reflux for 3 h. The mixture is then added slowly to 50 ml of MeOH and the resulting mixture is heated at 70° C. for 10 min to remove the methyl sulfide. Evaporation of solvent, washing twice with 50 ml of MeOH and evaporation of MeOH gives 1,3,5-tris (hydroxymethyl)benzene (6.96 g, 100%). $^1$H NMR (D$_2$O): δ 4.52 (6H, s), 7.15 (3H, s).

1,3,5-tris(bromomethyl)benzene (16)

To a suspension of 1,3,5-tris(hydroxymethyl)benzene (3.19 g, 18.98 mmol) in 75 ml of anhydrous ether at 0° C. is added dropwise a solution of phosphorus tribromide (7 ml, 74.4 mmol) in 7 ml of ether and the mixture is stirred for 1.5 h at 0° C. and 4 h at room temperature. The mixture is poured on ice and extracted with ether. The combined ether extracts are dried over Na$_2$SO$_4$ and evaporated to give 1,3,5-tris(bromomethyl)benzene 16 (6.35 g, 94%) as a white solid. $^1$H NMR (CDCl$_3$): δ 4.42 (6H, s), 7.33 (3H, s).

Tetraisopropyl 2-(3,5-bis(bromomethyl)phenyl)ethane-1,1-diphosphonate (17)

NaH (0.216 g, 5.4 mmol) is added at room temperature to a solution of tetraisopropyl methylenediphosphonate (1.77 g, 5.14 mmol) in 7 ml of anhydrous DMF and the suspension is stirred for 30 min under nitrogen. The resulting solution is transferred via a cannula to a solution of 1,3,5-tris (bromomethyl)benzene 16 (3.658, 10.2 nmol) in 8 ml of anhydrous DMF. The mixture is stirred for 1.25 h, quenched with a saturated solution of ammonium chloride and extracted with EtOAc (twice). The extracts are combined, washed with brine and dried over Na$_2$SO$_4$, filtered and concentrated in vacuo. The residue is purified by flash chromatography (silica gel, MeOH:CH$_2$Cl$_2$ /0:100–2:98) to furnish bisphosphonate 17 (2 g, 63%) as a colorless oil. IR (neat) 2975, 2930, 2870, 1721, 1673, 1602, 1450, 1380, 1370 cm$^{-1}$; $^1$H NMR (CDCl$_3$): δ 1.11 (6H, d, J=6.3 Hz), 1.14 (6H, d, J=6.2 Hz), 1.19 (12H, d, J=6.2 Hz), 2.37 (1H, tt, J=24, 6.2 Hz), 3.07 (2H, td, J=16.4, 6.2 Hz), 4.31 (4H, s), 4.62 (4H, m), 7.12 (3H, s); $^{13}$C NMR (CDCl$_3$): δ 23.63, 23.66, 23.69, 23.73, 23.79, 23.93, 24.00, 31.17 (t, J=4.9 Hz), 32.66, 40.42 (t, J=135 Hz), 70.94 (d, J=4 Hz), 70.98 (d, J=4 Hz), 71.11 (d, J=4 Hz), 71.28 (d, J=4 Hz), 127.57, 129.76, 138.00, 141.24 (t, J=7.5 Hz); MS (APCI) m/z (relative intensity) 623 ($^{81}$Br$^{81}$Br), 621 ($^{81}$Br$^{79}$Br), 619 ($^{79}$Br$^{79}$Br) (MH$^+$, 58, 100, 59), 579 (53), 537 (42), 495 (35), 453 (43); MS (FAB) m/z (relative intensity) 623 ($^{81}$Br$^{81}$Br), 621 ($^{81}$Br$^{79}$Br), 619 ($^{79}$Br$^{79}$Br) (MH$^+$, 36, 71, 36), 453 (82), 371(100); (MH$^+$, 46); HRMS calcd for C$_{22}$H$_{39}$O$_6$P$_2$Br$_2$ (MH$^+$) 619.0588, found 619.0589.

Tetraisopropyl 2-(3,5-bis(acetylthiomethyl)phenyl)ethane-1,1-diphosphonate (18)

To a solution of bisphosphonate 17 (2 g, 3.2 mmol) in 12 ml of anhydrous DMF under nitrogen is added at 0° C. via a cannula a solution of potassium thioacetate (1.1 g, 9.6 mmol) in 15 ml of anhydrous DMF. The mixture is stirred for 1.50 h at 0° C., quenched with water and extracted with EtOAc. The organic layer is dried over $Na_2SO_4$, filtered and evaporated. The residue is purified by flash chromatography (silica gel, $MeOH:CH_2Cl_2/0:100–2:98$) to give bisthioacetate 18 (1.38 g, 70%) as a light yellow oil. IR (neat) 2980, 2932, 2230, 1692, 1600 $cm^{-1}$; $^1H$ NMR ($CDCl_3$): δ 1.16 (6H, d, J=6.2 Hz), 1.18 (6H, d, J=6.2 Hz), 1.23 (12H, d, J=6.2 Hz), 2.26 (6H, s), 2.40 (1H, tt, J=24, 6.3 Hz), 3.07 (2H, td, J=16.5, 6.3 Hz), 4.00 (4H, s), 4.67 (4H, m), 6.95 (1H, s), 6.99 (2H, s); $^{13}C$ NMR ($CDCl_3$): δ 23.72, 23.75, 23.78, 23.84, 23.87, 23.90, 24.14, 30.25, 31.35 (t, J=4.8 Hz), 33.17, 40.59 (t, J=134 Hz), 70.98 (d, J=3 Hz), 71.01 (d, J=3 Hz), 71.15 (d, J=3 Hz), 71.28 (d, J=3 Hz), 127.24, 128.55, 137.62, 140.99 (t, J=7.6 Hz), 194.77; MS (APCI) m/z (relative intensity) 611 ($MH^+$, 100), 569 (63), 527 (58), 485 (37), 453 (31)); MS (FAB) m/z (relative intensity) 611 ($MH^+$, 100); HRMS calcd for $C_{26}H_{45}O_8P_2S_2$ ($MH^+$) 611.2031, found 611.2029.

2-(3,5-bis(thiomethyl)phenyl)ethane-1,1-diphosphonic acid (19)

A solution of bisthioacetate 18 (0.647 g, 1.06 mmol) in 20 ml of 6N HCl is heated to reflux under nitrogen for 6 h and cooled to room temperature. The solution is directly concentrated under high vacuum to afford the bisthiol diphosphonic acid 19 (0.373 g, 98%) as a amorphous solid. $^1H$ NMR ($D_2O$): δ 2.46 (1H, tt, J=23, 6.4 Hz), 3.00 (2H, td, J=16.6, 6.4 Hz), 3.55 (4H, s), 7.04 (3H, s); $^{13}C$ NMR ($D_2O$): δ 28.75, 31.41, 40.47 (t, J=126 Hz), 126.73, 127.99, 141.46, 142.74; MS (APCI) m/z (relative intensity) 359 ($MH^+$, 85), 325 (100); HRMS calcd for $C_{10}H_{17}O_6P_2S_2$ ($MH^+$) 358.9941, found 358.9942.

Bis-($PGE_2$)-bisphosphonate conjugate (20)

To a solution of bromide 13 (103 mg, 0.144 mmol) in dioxane (1 ml) at room temperature and under nitrogen is added dropwise via a cannula a solution of thiol 19 (25.8 mg, 0.072 mmol) and triethylamine (50 μl, 0.36 mmol) in water (0.5 ml) and the solution is stirred at room temperature for 2 h and concentrated. The residue is partitioned between EtOAc and water. The aqueous layer is washed twice with EtOAc and filtered on a cation exchange (DOWEX 50 $Na^+$ form). The filtrate is concentrated and the residue is purified by flash chromatography (silica gel C18, MeOH:water/0:100–60:40). The desired product comes eluted in the 30% and 60% methanol/water fractions which after lyophilisation give the desired conjugate 20 (44 mg, 52%) as a light yellow sticky solid. $^1H$ NMR ($D_2O$): δ 0.73 (6H, m), 1.17 (12H, m), 1.43 (4H, m), 1.54 (4H, m), 1.83 (4H, m), 1.98–2.20 (13H, m), 2.36 (2H, m), 2.63 (2H, dd, J=18.5, 7.6 Hz), 3.00 (2H, m), 3.05 (4H, s), 3.67 (4H, s), 3.98 (2H, m), 5.07–5.20 (4H, m), 5.32 (2H, m), 5.50 (2H, dd, J=15.4, 7.3 Hz), 5.61 (2H, dd, J=15.4, 8.4 Hz), 6.87 (1H, s), 7.17 (2H, s); $^{13}C$ NMR ($D_2O$): δ 14.57, 23.13, 25.33, 25.60, 26.80, 27.68, 32.03, 32.20, 33.57, 34.80, 36.57, 38.01, 42.15 (t, J=113 Hz), 53.41, 53.49, 55.11, 71.82, 77.50, 126.77, 128.04, 129.62, 131.99, 132.86, 134.97, 137.92, 144.66, 172.53, 183.67, 220.66; MS (FAB) m/z (relative intensity) 1230 ($[M+2Na]^+$, 0.8), 1208 ($[M+Na]^+$, 0.5), 379 (8), 114 (100).

EXAMPLE 6

Hydrolysis of conjugate 9 in rat plasma

In a typical experiment, a stock solution of conjugate 9 (50 μL, 18 μg, 0.02 μCi) is added to 1 ml solution of rat plasma (diluted to 50% with PBS) at 37° C. and the mixture is vortexed and incubated at 37° C. for 15 min, 1 h, 2 h and 4 h. At each time interval, 200 μL of the incubate is pipetted into a 1 mL Eppendorf vial and diluted with 200 μL acetonitrile. The suspension is centrifuged at 14K rpm for 3 min and 200 mL of the supernatant is pipetted into the silica gel column (preconditioned with either toluene or isopropyl alcohol). The column is then eluted with 2 mL methanol and the collect solution was counted on a Beckmann 2000 β-sintillation counter. The radioactivity obtained divided by the original loading represents the percentage of hydrolysis. The same experiments are carried out using 50% boiled plasma (diluted with PBS) as control and PBS as control.

EXAMPLE 7

Hydrolysis of conjugates 14, 15 and 20 in rat plasma

In a set of experiments essentially as described above but utilizing 100% rat plasma $^3H$-labelled conjugates 14 (36 μg, 0.1 μCi), 15 (38 μg, 0.1 μCi) and 20 (62 μg, 0.2 μCi) are incubated in fresh heperinized rat plasma at 37° C. Aliquots (100 μl) are worked up as before and the eluted $^3H$-label counted.

EXAMPLE 8

Characterization of $^3H$ liberated on hydrolysis of conjugate 20

A stock solution of 0.4 μCi conjugate 20 or $[^3H]$-$PGE_2$ (0.4 μCi) is incubated in either fresh rat plasma, boiled plasma or PBS (ml) at 37 C. After 4 h or 24 h, 100 μl aliquots are removed, diluted with acetonitrile (100 μl), vortexed and centrifuged. 100 μl of supernatant is separated by HPLC (C-18, 0.5% HOAc in water, 66%: acetonitrile 33%, 1 ml/min) with effluent monitored by an on-line scintillation detector and UV detector. No radioactivity is eluted under these conditions when 0.2 μCi, conjugate 20 (62 μg) is applied. (It is necessary to mix 0.4 mg of unlabelled 20 with 0.1 μCi labelled 20 to recover 0.05 μCi from the HPLC.) Radioactive peaks are identified by coelution with authentic $[^3H]$-$PGE_2$ and cold $PGA_2$. An authentic sample of $PGB_2$ is prepared by incubating $PGE_2$ (2.4 mg) with 1 ml rat plasma at 37° C. for 24 hr. The sample, purified by HPLC, will have appropriate $^1H$-NMR, UV and MS. To identify radioactive peaks eluting at the solvent front with incubation of conjugate 20 for 24 hr in fresh rat plasma, the fraction is collected and distilled. The collected distillate has 60% of the initial counts.

EXAMPLE 9

Binding of conjugate $[^3H]$-14 to human bone powder and release of label

Dual-labelled conjugate 14 ($[^3H]$-$PGE_2$/$[^{14}C]$-alendronate) (21.64 μCi of $^{14}C$ and 19.05 μCi of $^3H$) is placed in 1 ml 100% fetal bovine serum to yield a final concentration of 3.5 μM. 200 μM of this solution is incubated with 10 mg bone powder for 1, 2, 3 and 5 mins with vigorous shaking. The mixture is centrifuged (20 sec), 125 μl aliquot is taken from each sample and counted in 10 ml Atomlight in an LKB liquid scintillation counter, 125 μl of the radioactive sample is also counted at 0 time. The uptake of radioactivity into the bone powder is calculated by subtracting the dpms in the medium counted at the times indicated above from dpms at 0 time and this number is divided by the dpms at 0 time. The data demonstrates that about 76% of the $^{14}C$-moiety and 53% of the $^3H$-moiety are taken up by bone particles within 1 min.

Dissociation of $[^3H]$-$PGE_2$/$[^{14}C]$-alendronate from human bone powder in fetal bovine serum at 37 C is measured by incubating 10 mg of human one powder with 1 μl $[^3H]$-$PGE_2$/$[^{14}C]$-ABP in 1 ml FBS for 5 mins. The mixture is centrifuged (20 sec), 100 μl aliquot is taken and counted in Atomlight in an LKB liquid scintillation counter. The rest of the 900 μl solution is withdrawn, the bone powder is washed once with 1 ml phosphate buffered saline, 1 ml fresh fetal bovine serum is added and incubated with the bone powder for 15, 24, 39, 48, 59, 79 and 103 hours in a shaking bath at 37° C. 100 μl aliquots are withdrawn at these times and counted in 10 ml Atomlight in an LKB liquid scintillation counter. The release of radioactivity from the human bone powder into the medium is calculated as follows: dpms from 100 μl of the [$^3$H]-PGE$_2$/[$^{14}$C]-ABP at 5 mins are subtracted from dpms at 0 time. The resulting dpms reflect radioactivity taken up by bone powder. The dpms obtained by counting 100 μl aliquots at each time point are then divided by the dpms taken up by bone. 13% of the $^3$H-moiety is released into the medium at 15 hrs and by 103 hours 32.9% of the radioactivity is released into the medium. About 5% of the $^3$H moiety is released per day whereas the dpms of $^{14}$C-moiety in the medium are not significantly changed during this time frame.

EXAMPLE 10

In vivo uptake and release of [$^3$H]-14 in rats tibea and femora

Both compounds are administered i.v. via the tail vein to Sprague-Dawley female rats as a radiolabelled compound, equivalent to about 0.3 μCi/animal, [$^3$H]-alendronate is administered to nine rats and [$^3$H]-PGE$_2$/[$^{14}$C]-ABP (dual labelled conjugate 14), is administered to seven rats. After 1, 14 or 28 days, animals are sacrificed by $CO_2$ inhalation and the tibiae and femora are dissected, weighed and then stored at −20° C. The amount of radioactivity incorporated into the bone is determined by incineration in a Packard combuster after first air drying the bone for three days at ambient temperature. The percent of the compound retained in the skeleton at each time point is calculated on the basis of the radioactivity, converted to nmoles/gm bone on the assumption that the skeleton represents 8% of the body weight. The skeletal retention is expressed as percent administered dose.

EXAMPLE 11

In vivo assay of conjugate 14 in a rat model of osteoporosis

Briefly, three month old Sprague-Dawley rats are ovariectomized and are kept for eight weeks prior to the start of treatment to allow the development of osteopenia. Treatment groups receive 10 or 100 mg/kg 14, i.v. (see table below). Control groups include: an ovariectomized vehicle treated group, a sham operated non-ovariectomized group, group 4 receiving equimolar doses of non-conjugated bisphosphonate (NCB), i.e. 4-carboxymethylthiobutane-1,1-diphosphonic acid disodium salt, plus PGE$_2$, and group 5 PGE$_2$ alone. All animals are treated for four weeks.

| 1) Ovx | vehicle tx | saline i.v. | 1× per week |
|---|---|---|---|
| 2) Ovx | 14 | 100 mg/kg i.v. | 1× per week |
| 3) Ovx | 14 | 10 mg/kg i.v. | 1× per week |
| 4) Ovx | NCB + PGE$_2$ | ~5 mg/kg each i.v. | 1× per week |
| 5) Ovx | PGE$_2$ | 6 mg/kg s.c. | 5× per week |
| 6) Sham-Ovx | vehicle tx | saline s.c. | 5× per week |

Animals receive the fluorescent bone label calcein (20 mg/kg i.p.) 14 and 4 days prior to sacrifice. Femora, tibiae and vertebrae are removed and fixed in 70% EtOH. The femoral bone mineral content (BMC) is measured using a HOLOGIC QDR 4500A x-ray densitometer. Femoral length is also measured. Tibiae are processed without decalcification through increasing concentrations of EtOH and embedded in methylmethacrylate using a Hypercenter XP tissue processor. Five micron thick Masson's Trichrome stained sections are used to measure the following static histomorphometric variables of cancellous bone structure. Bone volume/tissue volume (BV/TV, %), trabecular number (Tb.N, #/mm), trabecular thickness (TbTh., μm), trabecular separation (TbSp., μm) are measured or calculated directly from primary measurements of tissue area, trabecular bone area, and trabecular bone perimeter.

Ten micron thick sections are coverslipped unstained for dynamic fluorochrome label measurements. Viewed under epifluorescence the length of calcein labeled bone surfaces and the interlabel distances are measured. The mineralizing surface (MS/BS, %) is calculated as one-half the length of single labeled surface plus the length of the double labeled surface expressed as a percentage of total bone surface. This measures the relative amount of bone surface undergoing formation. The mineral apposition rate (MAR, μm/day) is calculated as the mean of equidistant points between the first and second label divided by the labeling interval (14 days) and estimates the cell based formation rate. Bone formation rate surface referent (BFR, BS, μm$^3$/μm$^2$/yr) or the estimated 3D volume of bone formed per measured 2D bone area is calculated as the product of mineral apposition rate (MAR) and the mineralizing surface (MS) expressed per year.

The anti-resorptive effect of NCB, the bisphosphonate core of 14 is also evaluated using the growing rat model (Schenk Assay). Using this model rats are treated s.c. for ten days at 0, 3, or 30 mg/kg. After necropsy, femora are measured for length and incinerated at 700° C. for 24 hours. Inhibition of bone resorption in long bones (femur) of growing rats results in increased bone mineral content measured as femoral ash weight corrected for length (mg/mm).

Statistical analysis is done using the Statview (Macintosh) package. Differences between two groups are tested using Students-t test. With three or more groups, differences are tested using one-way analysis of variance (ANOVA). If significance is found, the differences in group means are tested using the Fisher PLSD with a p<0.05 considered significant.

All of the above examples can be modified by one of ordinary skill in the art to measure the activity of the compounds encompassed by the instant invention.

What is claimed is:

1. A compound selected from the group consisting of:

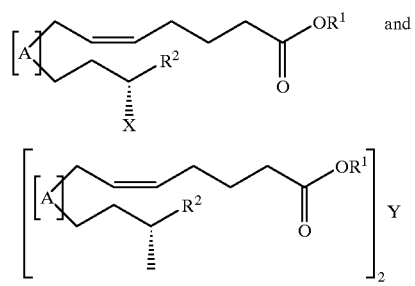

and mixtures thereof and the pharmaceutically acceptable salts thereof, wherein:

A is a dioxygenated cyclopentane moiety selected from the group consisting of:

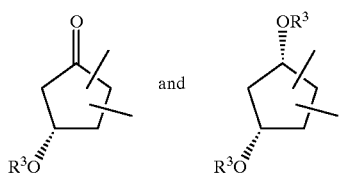

X is selected from the group consisting of:

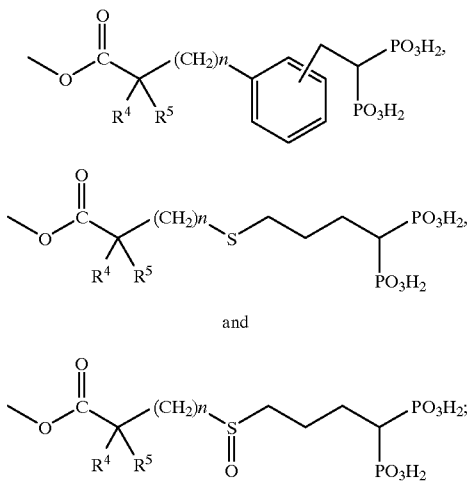

Y is selected from the group consisting of:

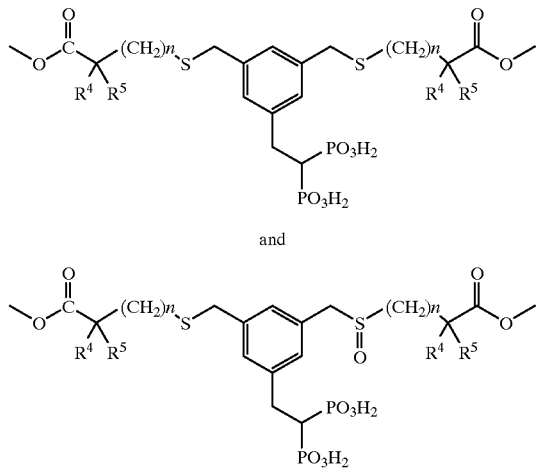

$R^1$ is selected from the group consisting of H, C1–C10 alkyl, and $Si(CH_3)_2tBu$;

$R^2$ is selected from the group consisting of H and $C_{1-10}$ alkyl;

$R^3$ is selected from the group consisting of H, tetrahydropyran, and $Si(CH_3)_2tBu$;

$R^4$ and $R^5$ are independently selected from the group consisting of H, C1–C10 alkyl, phenyl, benzyl, C1–C10 alkoxy, and $CF_3$, and n is an integer from 0 to 5.

2. A compound of the formula:

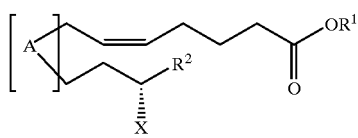

and mixtures thereof and the pharmaceutically acceptable salts thereof, wherein:

A is a dioxygenated cyclopentane moiety selected from the group consisting of:

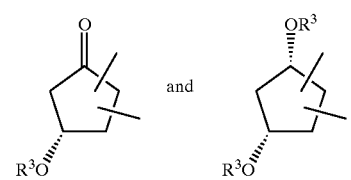

X is selected from the group consisting of:

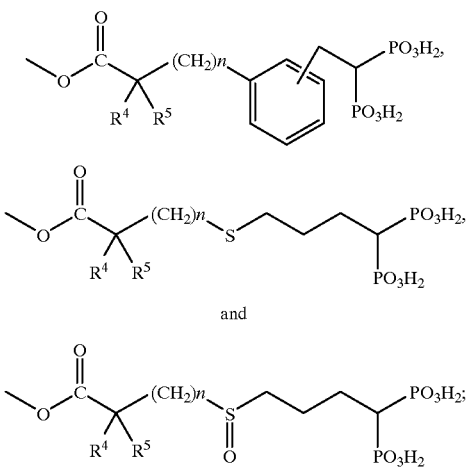

$R^1$ is selected from the group consisting of H, C1–C10 alkyl, and $Si(CH_3)_2tBu$;

$R^2$ is selected from the group consisting of H and $C_{1-10}$ alkyl;

$R^3$ is selected from the group consisting of H, tetrahydropyran, and $Si(CH_3)_2tBu$;

$R^4$ and $R^5$ are independently selected from the group consisting of H, C1–C10 alkyl, phenyl, benzyl, C1–C10 alkoxy, and $CF_3$, and n is an integer from 0 to 5.

3. A compound according to claim 2 wherein X is selected from the group consisting of:

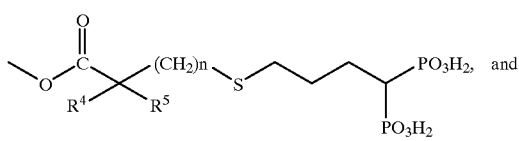

-continued

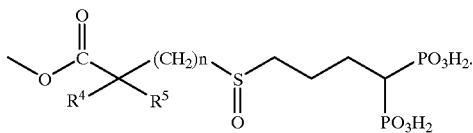

4. A compound according to claim 3 wherein X is

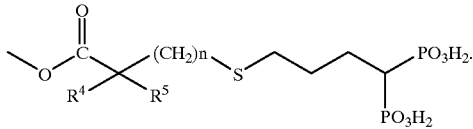

5. A compound according to claim 4 wherein n is zero and $R^4$ and $R^5$ are each H.

6. A compound according to claim 5 wherein A is

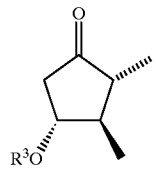

7. A compound according to claim 6 wherein $R^1$ and $R^3$ are H.

8. A compound according to claim 7 wherein $R^2$ is n-$C_5H_{11}$.

9. A pharmaceutical composition comprising a compound according to claim 1 and a pharmaceutically acceptable carrier.

10. A method of inhibiting bone resorption in a mammal comprising administering to a mammal in need thereof a therapeutically effective amount of a compound according to claim 1.

11. A method according to claim 10 wherein said mammal is a human.

12. A method for treating or reducing the risk of contracting a disease state or condition in a mammal associated with bone resorption comprising administering to said mammal a theraperutically effective amount of a compound according to claim 1.

13. A method according to claim 12 wherein said mammal is a human.

14. A method according to claim 13 wherein said disease state or condition is selected from the group consisting of osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

15. A method according to claim 14 wherein said disease state or condition is osteoporosis or glucocorticoid induced osteroporosis.

16. A method of increasing the bone fracture healing rate in a mammal comprising administering to a mammal in need thereof a therapeutically effective amount of a compound according to claim 1.

17. A method for enhancing the rate of successful bone grafts in a mammal comprising administering to a mammal in need thereof a therapeutically effective amount of a compound according to claim 1.

18. A method of enhancing the rate of bone formation in a mammal comprising administering to a mammal in need thereof a therapeutically effective amount of a compound according to claim 1.

* * * * *

UNITED STATES PATENT AND TRADEMARK OFFICE
CERTIFICATE OF CORRECTION

PATENT NO.    : 6,121,253
DATED         : September 19, 2000
INVENTOR(S)   : Yongxin Han, Robert N. Young, Laurent Gil and Rejean Ruel It is certified that error appears in the above-identified patent and that said Letters Patent is hereby corrected as shown below:

Column 4,
Lines 25-35, delete the structures and insert therefor the following structures:

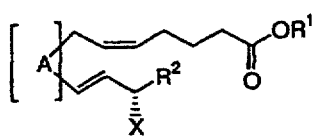

and

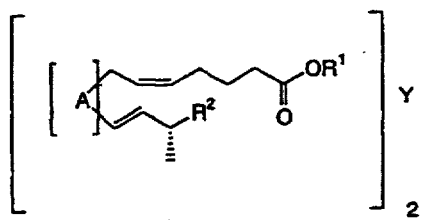

Column 6,
Lines 32-44, delete the structures and insert therefor the following structures:

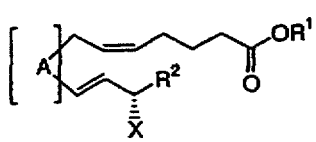

and

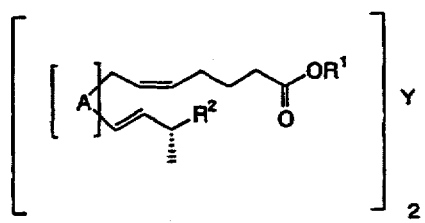

UNITED STATES PATENT AND TRADEMARK OFFICE
CERTIFICATE OF CORRECTION

PATENT NO.   : 6,121,253
DATED        : September 19, 2000
INVENTOR(S)  : Yongxin Han, Robert N. Young, Laurent Gil and Rejean Ruel It is certified that error appears in the above-identified patent and that said Letters Patent is hereby corrected as shown below:

Column 7,
Lines 50-55, delete the structure and insert therefor the following structure:

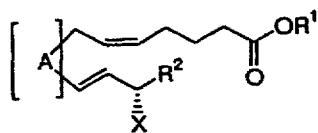

Column 28, claim 1,
Lines 50-60, delete the structures and insert therefore the following structures:

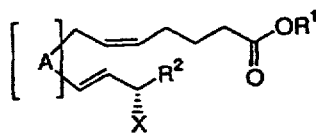

and

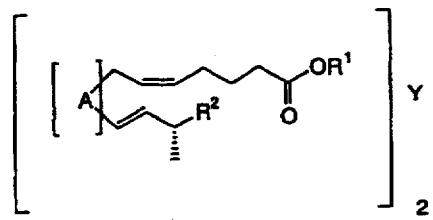

UNITED STATES PATENT AND TRADEMARK OFFICE
CERTIFICATE OF CORRECTION

PATENT NO. : 6,121,253
DATED : September 19, 2000
INVENTOR(S) : Yongxin Han, Robert N. Young, Laurent Gil and Rejean Ruel It is certified that error appears in the above-identified patent and that said Letters Patent is hereby corrected as shown below:

Column 30, claim 2,
Lines 5-10, delete the structure and insert therefor the following structure:

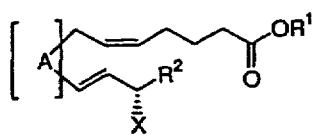

Signed and Sealed this

Fourth day of December, 2001

Attest:

NICHOLAS P. GODICI
Attesting Officer      Acting Director of the United States Patent and Trademark Office